US00PP08437P

United States Patent [19]

Drewlow

[11] Patent Number: Plant 8,437

[45] Date of Patent: Oct. 26, 1993

[54] IMPATIENS PLANT NAMED IMPULSE

[75] Inventor: Lyndon W. Drewlow, Ashtabula, Ohio

[73] Assignee: Mikkelsens, Inc., Ashtabula, Ohio

[21] Appl. No.: 858,393

[22] Filed: Mar. 26, 1992

[51] Int. Cl.[5] ..... A01H 5/00

[52] U.S. Cl. ..... Plt./87.6

[58] Field of Search ..... Plt./87.6

*Primary Examiner*—James R. Feyrer

*Assistant Examiner*—E. F. McElwain

*Attorney, Agent, or Firm*—Foley & Lardner

[57] ABSTRACT

A distinct cultivar of Impatiens plant named Impulse, characterized particularly by its relatively large, deep bright pink flowers, bright green leaves, with slight cream variegation around midrib at base on older leaves under high light conditions, excellent self-branching, early flowering, and floriferous habit.

1 Drawing Sheet

The present invention relates to a new and distinctive cultivar of Impatiens plant, botanically known as Impatiens, commercially known as New Guinea Impatiens, and known by the cultivar name Impulse. Impulse was developed by me through controlled breeding by crossing Mikkelsen Seedling No. 87-691-1 (seed parent) with Mikkelsen Seedling No. 89-453-3 (pollen parent) both of which are proprietary.

Asexual reproduction by terminal or stem cuttings, in greenhouses in Ashtabula, Ohio, has shown that the unique features of this new Impatiens are stabilized and are reproduced true to type in successive propagations.

The following combination of characteristics distinguish the new Impatiens from both its parent varieties and other cultivated Impatiens of this type known and used in the floriculture industry. The characteristics are described with reference to the cultivar Gemini, disclosed in U.S. Plant Pat. No. 5,132, which is believed to be the most relevant cultivar for comparison purposes.

1. Impulse has deep bright pink flowers (between 58C and 61D) while Gemini has bright pink flowers (55B) that are lighter in color.
2. Impulse has larger flowers (6.5 to 7.0 cm in diameter) than the flowers of Gemini (5.5 to 6.0 cm in diameter).
3. Impulse has flower pedicels that are light green in color with a slight reddish tint, while Gemini has reddish colored pedicels.
4. Impulse and Gemini both have bright green leaves. However, Gemini has much more cream colored variegation around midrib than Impulse.
5. Impulse has a stem color which is generally light green but reddish just above each internode, while Gemini has a reddish purple stem.
6. Impulse is 7 to 10 days earlier in flowering than Gemini.
7. The midrib on Gemini is much deeper red in color than Impulse which has a pinkish tint on top of leaf. Also, the underside of the midrib of Impulse is green while Gemini is a reddish color which carries out to major veins.
8. Impulse has large leaves, measuring 15 to 18 cm long by 4 to 5 cm wide, while Gemini has leaves which are 11 to 12 cm long and 3.5 to 4.0 cm wide.
9. Impulse is a more self-branched upright growing plant than Gemini, which is a more open spreading type of plant.
10. Self-branching and early flowering of Impulse allows the cultivar to be grown in 10 cm pots. However, Impulse is vigorous enough so it can be grown in 15 to 25 cm containers as well. This flexibility is important to the grower.

The accompanying color photograph is a front perspective view illustrating the overall appearance of Impulse. The colors are as true as it is reasonably possible to obtain in a colored reproduction of this type. The photograph was taken on Apr. 15, 1991, under natural light on an overcast day, under double poly greenhouse covering at Ashtabula, Ohio.

The following is a detailed description of my new cultivar, based on plants produced in greenhouses in Ashtabula, Ohio during the Fall and early Winter seasons of the year. Plants were grown in 10 cm pots and measurements were taken 12 weeks after rooted cuttings were planted. Height measurements were taken from the soil line of the container. The plants were grown at 65°-68° F. night temperatures, under 3000-4000 foot candles of light, and with nutritional values of 250 ppm nitrogen, 75 ppm potassium, and 250 ppm phosphorous, with trace elements added. Habit of growth, foliage coloration, leaf variegation, size of leaves and flower size will be influenced by nutritional and environmental conditions, without, however, any variation in the phenotype.

Color references are made to The Royal Horticultural Society Colour Chart except where general terms of ordinary dictionary significance are used.

Parentage: A controlled cross between female parent Mikkelsen Seedling No. 87-691-1 and male parent Mikkelsen Seedling No. 89-453-3.

Propagation:

A. *Type cutting.*—Stem tip 15 mm long will develop to 4 to 5 cm long in 18 to 21 days.

B. *Time to root.*—8 to 10 days at 23° C. summer; 10 to 12 days at 20° C. winter.

C. *Rooting habit.*—Heavy, fibrous.

Plant description:

A. *Form and habit of growth.*—Semi-upright to mounded; highly self-branched; intermediate in height; flowers carried over the top of leaf canopy; continuous flowering, vigorous growing flowering herb.

B. *Foliage description.*—Bright deep green with reddish purple midrib on mature leaves. Trace of cream variegation around midrib at leaf base on older leaves exposed to high light conditions. 1. Size: 15 to 18 cm long and 4 to 5 cm wide for average mature leaf. 2. Shape: Lanceolate with acuminate apex and acute base. 3. Texture: Both upper and lower surfaces are glabrous. 4. Margin: Finely serrated with fine ciliate. 5. Color: Young foliage, top side 137B. under side 138B. mature foliage, top side 137A. under side 138B. 6. Venation: Pinnate, green.

Flowering description:

A. *Flowering habits.*—Flowers continuously from leaf whorl in a progressively orderly manner with one flower per leaf axil. When the last flower in a leaf whorl opens the first flower in the leaf whorl above starts to open. It takes 5 to 7 days for a mature bud to fully open and then the flower may last two weeks or longer depending on the environment.

B. *Natural flowering seasons.*—Indeterminant and continuous. Quantity of flowering increases with increasing levels of light.

C. *Flower buds.*—Ellipsoidal, flowers perfect, reddish spur 5.0 to 5.5 cm long with green tip on mature bud, with the throat behind the ovary and originating from the major sepal.

D. *Flowers borne.*—On individual light green pedicels (with slight reddish tint) 5.0 to 6.0 cm long from a whorl of usually 5 leaves, flowering progressively around the whorl as buds and leaves develop. Leaf axils have one flower each.

E. *Quantity of flowers.*—Very floriferous because of highly self-branched nature of plant and long lasting flowers. Flower development is continuous and above leaf canopy.

F. *Diameter of flower.*—6.5 to 7.0 cm.

G. *Petals.*—1. Shape: Heart, standard is largest. 2. Color: Top side in winter when opening, between 61D and 58C, fading to 68B; underside 61D. 3. Number of petals: 5. 4. Size of petals: Standard: 4.0 cm wide by 3.0 cm long; two equal lobes, shallow cut. Wings: 2.5 cm wide by 3.25 cm long; two equal lobes, intermediate cut. Keel: 3.0 wide by 3.5 cm long; two unequal lobes, deep cut.

H. *Reproductive organs.*—1. Stamens: Five (5) in number. a. Anther shape: Hooded, color cream with reddish tint. b. Pollen color: Cream. 2. Pistils: a. Stigma shape: Five segmented column, color cream. b. Style color: Cream. c. Ovaries: Five (5) in number, size 4 mm when receptive, color green.

Disease resistance: No significant disease or insect problems to date.

Other important characteristics: Impulse has demonstrated the ability to tolerate both high temperatures and sunlight and continue to bloom, as well as cool temperatures (40°-50° F.). Thus the growing season has been expanded, a great advantage to growers.

I claim:

1. A new and distinct Impatiens plant named Impulse, as illustrated and described.

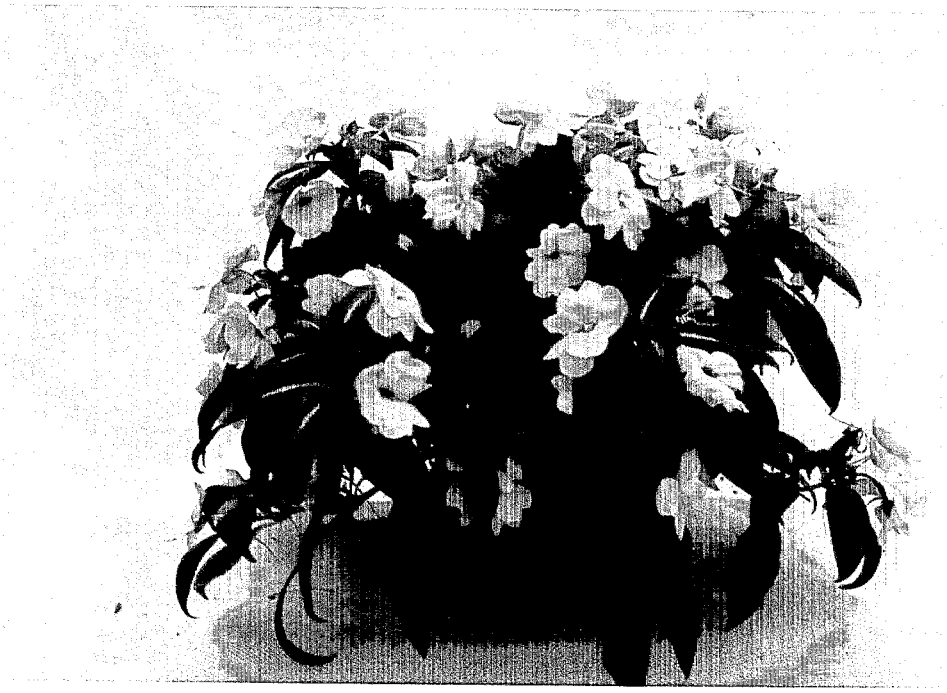

* * * * *